US00PP21883P2

(12) United States Plant Patent
Miksich

(10) Patent No.: US PP21,883 P2
(45) Date of Patent: Apr. 26, 2011

(54) ***HIBISCUS* PLANT NAMED 'PINK ELEPHANT'**

(50) Latin Name: ***Hibiscus* hybrid (L.)**
Varietal Denomination: Pink Elephant

(76) Inventor: Thomas M. Miksich, Crown Point, IN (US)

( * ) Notice: Subject to any disclaimer, the term of this patent is extended or adjusted under 35 U.S.C. 154(b) by 397 days.

(21) Appl. No.: 12/229,143

(22) Filed: Aug. 20, 2008

(51) Int. Cl.
*A01H 5/00* (2006.01)

(52) U.S. Cl. ..... Plt./257

(58) Field of Classification Search ..... Plt./257
See application file for complete search history.

*Primary Examiner* — Susan B McCormick Ewoldt

(57) ABSTRACT

A new and distinct hybrid of hardy *Hibiscus* plant named 'Pink Elephant' producing a multitude of large, flat, pink flowers with small maraschino cherry red eye and light rose veining on large plants over at least 12 weeks during the summer and early fall.

2 Drawing Sheets

Botanical classification: *Hibiscus* hybrid (L.).
Variety denomination: 'Pink Elephant'.

BACKGROUND AND ORIGIN OF THE PLANT

The present invention relates to the new and distinct hardy *hibiscus* plant, *Hibiscus* 'Pink Elephant', also referred to as the "new plant," hybridized by Thomas M. Miksich in the mid1980's at the hybridizer's previous residence in East Chicago, Ind. and selected for further evaluation two years later. The new plant is a cross between an unnamed *H. moscheutos* hybrid, and an unnamed hybrid of *H. coccineus*. *Hibiscus* 'Pink Elephant' has been propagated both by stem cuttings and division of the crown at the hybridizer's current residence in Crown Point, Ind. The resultant asexually propagated plants have been found to be stable and true to type in successive generations.

SUMMARY OF THE PLANT

*Hibiscus* 'Pink Elephant' differs from all other *hibiscus* known to the applicant in the following traits:

1. Large, flat, pink flowers with small maraschino cherry red eye and light rose veining.
2. Flowers are held out from the plant with little or no drooping.
3. Large plant habit.
4. Continuous or repeat blooming over a long season.

The foliage shape of 'Pink Elephant' is variable, depending on the time of year and position on the stem. The new plant is most similar to *Hibiscus* 'Pink Wonder' U.S. Plant Pat. No. 9,555 but is distinct in that the flower of 'Pink Elephant' has a smaller eye zone diameter, lighter pink petals, lighter rose colored veining in the petals and light cream colored stigma.

*Hibiscus* 'Pink Elephant' is more floriferous and has larger flowers than either of its parents. It could be most closely compared to 'Morrison-Gilberg (VII)' and in doing so the new plant has darker pink flowers with more overlapping petals and also flowers for a longer period of time.

BRIEF DESCRIPTION OF THE DRAWINGS

The photographs of the new plant demonstrate the unique traits of 'Pink Elephant' and the overall appearance of the plant. The colors are as accurate as reasonably possible with color reproductions. Variation in ambient light spectrum, source and direction may cause the appearance of minor variation in color.

DETAILED BOTANICAL DESCRIPTION

Figure 1:
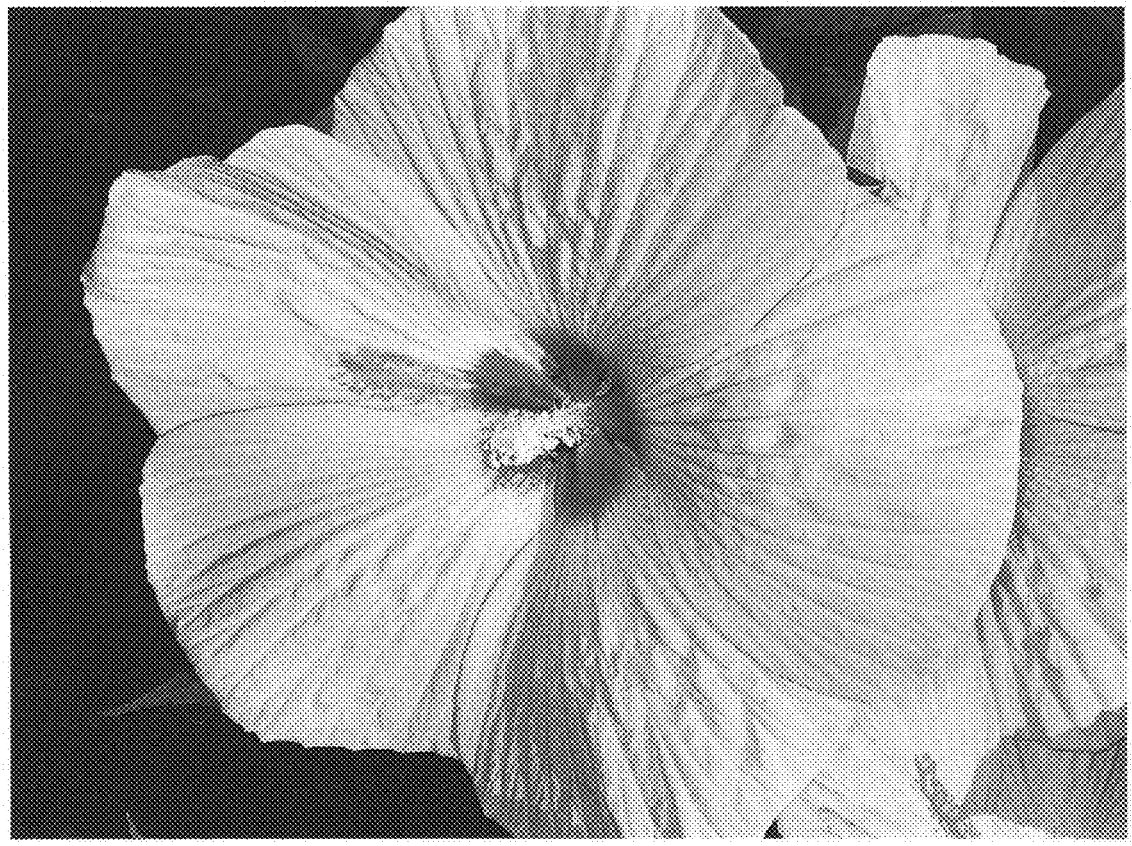
FIG. 1 shows a close-up of the flower.
Figure 2:
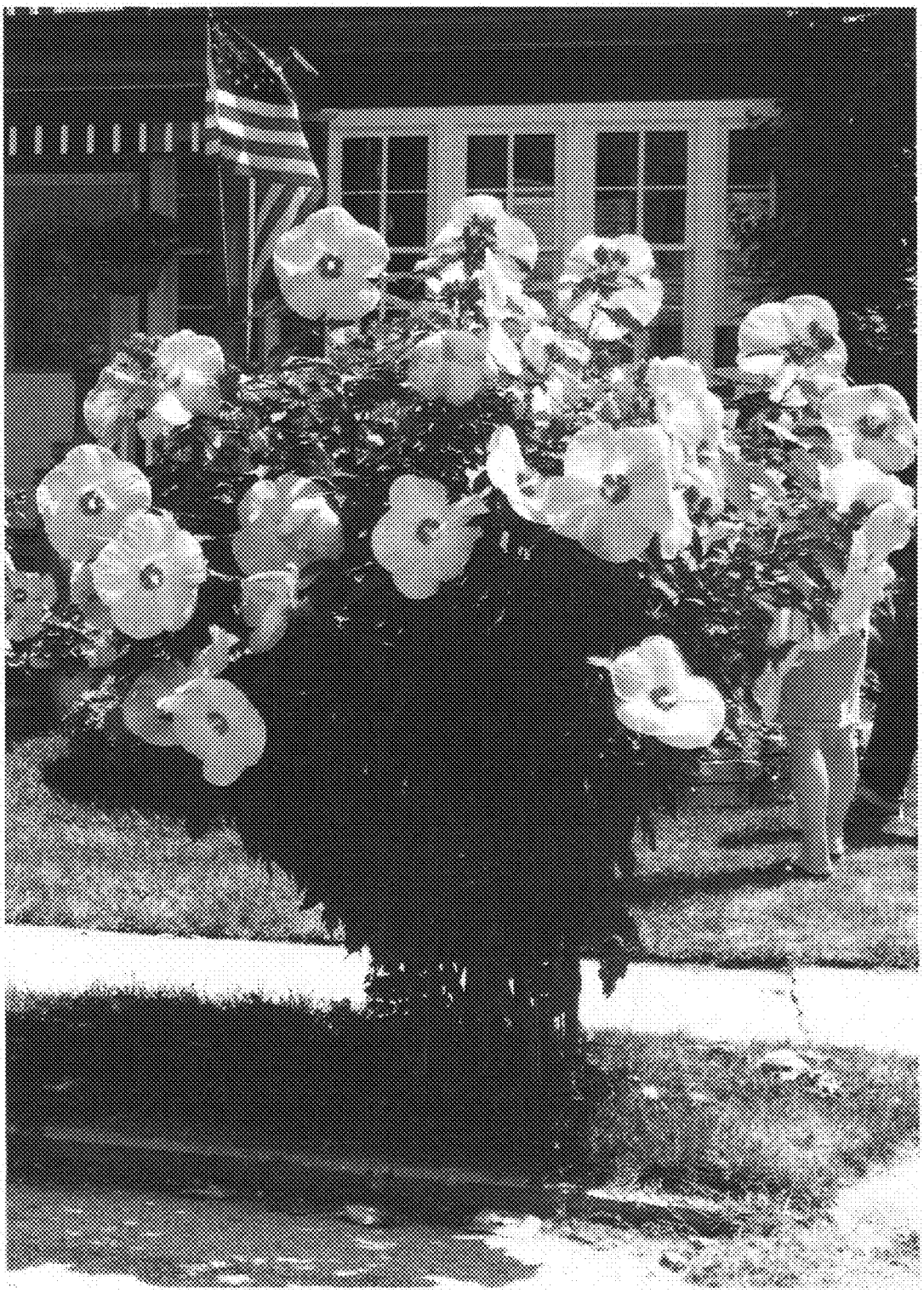
FIG. 2 shows the plant in full flower in mid season.

The following descriptions and color references are based on the 2001 edition of The Royal Horticultural Society Colour Chart except where common dictionary terms are used. *Hibiscus* 'Pink Elephant' has not been observed under all possible environments. The phenotype may vary slightly with different growing environments such as temperature, light, fertility, moisture and maturity levels, but without any change in the genotype. The following observations and size descriptions are of an eight-year old plant in the garden of the hybridizer in Crown Point, Ind. with supplemental fertilizer and water as needed. The plants were not treated with grow regulators to reduce their normal height.

Botanical classification: *Hibiscus* hybrid.

Parentage: Female parent *Hibiscus moscheutos* of unknown heritage times unknown hybrid of *H. coccineus* (male parent);

Propagation method: Stem cuttings and division; Time to initiate roots from cuttings about three weeks.

Rooting habit: Normal, thick to about 4 cm diameter, fleshy, branching; root color tan to creamy white.

PLANT DESCRIPTION

Plant shape and habit: Multi-stemmed hardy herbaceous perennial with 12 to 18 thick upright branched main stems producing rounded mound;

Crop time: Under normal summer growing conditions 12 to 18 weeks to flower in a four-liter container. Plant growth rate is very good.

Plant size: Unpinched plant stems without growth regulators about 188 cm tall from soil line and overall plant width at the widest point about 200 cm;

Internode length: Unpinched plant about 9 cm; pinched plant about 7 cm;

Foliage description: Opposite; dentate; variable with leaves entire to palmately lobed with three to five lobes, but typically palmate with center lobe much larger than other two or four lobes; color nearest RHS 137A on top and nearest RHS N138A underneath; blade up to 18 cm long and 15 cm wide at broadest point;

Veins: Palmate, between RHS 138C with some tinting of RHS 184D of the main vein on the top surface and nearest RHS 145C underneath;

Petioles: 5 to 10 cm long and 5 mm wide; glaucous, glabrous, nearly round to concave top surface near base; RHS 185B on top with direct sunlight and nearest RHS 144A underneath.

FLOWER DESCRIPTION

Buds: One day prior to opening about 10 cm long and 4 cm in diameter, acute apex and bluntly rounded base, unopened petals RHS 63A at apex and veins with petal area between veins at base nearest RHS 64D; prior to petals showing buds are about 4.5 cm long and 3 cm in diameter, ovoid with acute apex; color between RHS 144A and RHS 144B with veins RHS 144A;

Epicalyx: Entire, smooth, glabrous, linear with sharply acute apex; 10 to 12 per flower; 3.5 cm long tapering to base of 3 mm wide; RHS 144A on both inner and outer surface;

Sepals: Five, fused in lower half forming tubular star-shaped calyx; glabrous, acute apex; about 5 cm long and 2.5 cm wide at fused portion; RHS 144A;

Flowers: Solitary, flat, outwardly facing; about 30 cm across, smaller later in flowering season; persist for a one to two days; effective for at least 12 weeks beginning mid July with a repeat flowering in the fall lasting into October; no detectable fragrance;

Petals: Five; basally adnate to the androecium, imbricate to about 70% overlapping at widest part (only 30% of each petal not being overlapped by the two petals on either side); 15 cm long and 18 cm wide at broadest span; inside face RHS 68B with veins near center of RHS 68A; veins near edge of petals same color as petal; central eye pattern 6 to 7 cm across consisting of the inside 3 cm portion of the petals and feathering out in the last 3 cm of eye; petal portion outside of eye matte texture; eye: shiny texture, color nearest RHS 45A; back of petals between RHS 63B and RHS 63C near outer edge and gradually lightening toward petal base between RHS 62C and RHS 62D; veins in center of petal back RHS 64B and lightening toward center to RHS 62D; veins on back same color as petal near apex;

Gynoecium: Style: enclosed in column; white, lighter than RHS 11D, 5 to 8 cm long and 2 mm diameter; split into five branches in the distal 12 to 15 mm;

Stigma: 2 mm in diameter, nearest RHS 19C with slight pinkish tint about RHS 64D around outside perimeter;

Androecium: Filaments: numerous, about 120; less than 1 mm in diameter and about 5 mm long; attached to entire length of column; lighter than RHS 65D;

Anthers: Round prior to anthesis, like two circular tubes connected in between by a membranous layer, about 2 mm in diameter on the round side and 1 mm thick; nearest RHS 47A on the perimeter and RHS 50D in the center;

Pollen: Numerous, round with microscopic points, shiny, less than 0.1 mm long, nearest RHS 11D.

Pedicel: Glabrous, rounded, very slightly curved, length from base of bud to abscission point about 2.0 cm long and 4 mm wide on early flowers; RHS 138A;

Peduncle: Flowers are held out easily visible by up to 8 cm long and 3 mm wide; glabrous, nearest RHS 137D with some tinting of RHS 59D;

Fruit: Five-valved capsule, longitudinally dehiscing; with swollen calyx; glabrous; globose, occasionally with abruptly acute apex; between RHS N199B and RHS N199C when mature;

Seed: Floccose, globose to slightly reniform; 3 mm in diameter, RHS 200A;

Disease resistance: Resistance beyond that of other hardy *hibiscus* cultivars has not been observed. The plant grows best with plenty of moisture and adequate drainage, but is able to tolerate some drought when mature. Hardiness at least from USDA zone 4 through 9, and other disease resistance is typical of that of other *hibiscus* cultivars.

I claim:

1. A new and distinct hybrid cultivar of hardy *Hibiscus* plant named 'Pink Elephant' as herein described and illustrated, producing a multitude of large pink flowers with maraschino cherry eye on large plants over at least 12 weeks during the summer and early fall, suitable as a potted plant, for the garden, and for cut flower arrangements.

* * * * *

HIBISCUS PLANT NAMED 'PINK ELEPHANT'

HIBISCUS PLANT NAMED 'PINK ELEPHANT'